United States Patent
Knuth et al.

(10) Patent No.: US 7,121,815 B2
(45) Date of Patent: Oct. 17, 2006

(54) TUBE COUPLING FOR A PERISTALTIC PUMP

(75) Inventors: Reinhard Knuth, Melsungen (DE); Ronald Lutz, Stolberg (DE); Bodo Schacht, Malsfeld (DE)

(73) Assignee: B. Braun Melsungen AG, (DE)

( * ) Notice: Subject to any disclaimer, the term of this patent is extended or adjusted under 35 U.S.C. 154(b) by 431 days.

(21) Appl. No.: 10/600,729

(22) Filed: Jun. 20, 2003

(65) Prior Publication Data

US 2004/0022655 A1 Feb. 5, 2004

(30) Foreign Application Priority Data

Jun. 21, 2002 (DE) .......................... 202 09 663 U

(51) Int. Cl.
*F04B 43/08* (2006.01)
(52) U.S. Cl. ................ 417/477.1; 417/477.2; 604/153
(58) Field of Classification Search ............ 417/477.2, 417/477.1, 474, 63; 138/104; 285/242, 285/417, 418, 419, 420; 604/153
See application file for complete search history.

(56) References Cited

U.S. PATENT DOCUMENTS

| | | | | |
|---|---|---|---|---|
| 255,335 A | * | 3/1882 | Rix | ........................ 285/148.17 |
| 911,267 A | * | 2/1909 | Pittman | .................... 285/154.3 |
| 3,565,554 A | | 2/1971 | Muller | |
| 4,270,777 A | * | 6/1981 | Fisher | ......................... 285/242 |
| 4,391,600 A | * | 7/1983 | Archibald | .................... 604/153 |
| 5,182,954 A | * | 2/1993 | Menheere | ................ 73/864.45 |
| 5,215,450 A | | 6/1993 | Tamari | |
| 5,242,279 A | * | 9/1993 | Knuth | ......................... 417/474 |
| 5,983,949 A | * | 11/1999 | Pohle | ......................... 138/104 |
| 6,213,996 B1 | * | 4/2001 | Jepson et al. | ............... 604/533 |
| 6,224,571 B1 | * | 5/2001 | Bierman | ..................... 604/174 |
| 6,261,262 B1 | * | 7/2001 | Briggs et al. | ............... 604/153 |

FOREIGN PATENT DOCUMENTS

| | | | |
|---|---|---|---|
| DE | 84 06 203 | * | 5/1984 |
| DE | 4126088 | | 1/1993 |
| DE | 29720382 | | 10/1998 |

* cited by examiner

*Primary Examiner*—Charles G. Freay
(74) *Attorney, Agent, or Firm*—Osha Liang LLP; John W. Montgomery

(57) ABSTRACT

An infusion pump has a housing (10) accommodating a pump finger mechanism (12). The pump finger mechanism (12) acts on a pump hose (13) fastened at holders (16, 21) of the housing. The pump hose (13) is supported by a door (24). In order to facilitate proper and positionally correct placement of the pump hose, one of the holders (16) includes an oblique pin. The associated transition piece (15) of the pump hose (13) has a hole (18) with the same inclination angle as the oblique pin. The other transition piece (20) is of a different structure so that the transition pieces cannot be mixed up. A longitudinal color strip (29) on the pump hose is provided to visually indicate any twisting of the hose.

22 Claims, 2 Drawing Sheets

TUBE COUPLING FOR A PERISTALTIC PUMP

RELATED APPLICATIONS

This application claims priority from German Patent Application No. 202 09 663.7, filed on Jun. 21, 2002.

FIELD OF INVENTION

The invention refers to an infusion pump comprising a pump hose with respective transition pieces at opposite ends, a housing accommodating a pump finger mechanism and having two holders for attaching the two transition pieces, and a door provided at the housing which forms a counter bearing for supporting the pump hose.

DESCRIPTION OF RELATED ART

From teachings in DE 8406203 U1, co-owned with the present application, an infusion pump is known comprising a housing for accommodating an exchangeable pump hose. A housing is provided with a pump finger mechanism continually squeezing the hose from top to bottom, thereby causing a volumetric conveying of the liquid contained in the pump hose. The pump hose is made of a relatively soft flexible material, especially silicone, its two ends being equipped with transition pieces to which a supply hose and a discharge hose of flexible plastics material respectively, are connected. The housing in provided with holders into which the transition pieces are hooked. In this manner, it is possible to attach the pump hose to the housing in a defined manner. Both holders and the associated transition pieces are designed such that the upper transition piece only fits into the upper holder and the lower transition piece only fits into the lower holder. However, the length of the pump hose allows a twisting of the pump hose, where, for example, the lower holder is twisted by 360° with respect to the upper holder. This bears the risk of a greater deviation from the set output volume or, in the worst case, a free flow.

DETAILED DESCRIPTION

The following is a detailed description of an embodiment of the invention with reference to the drawings.

Figure 1:
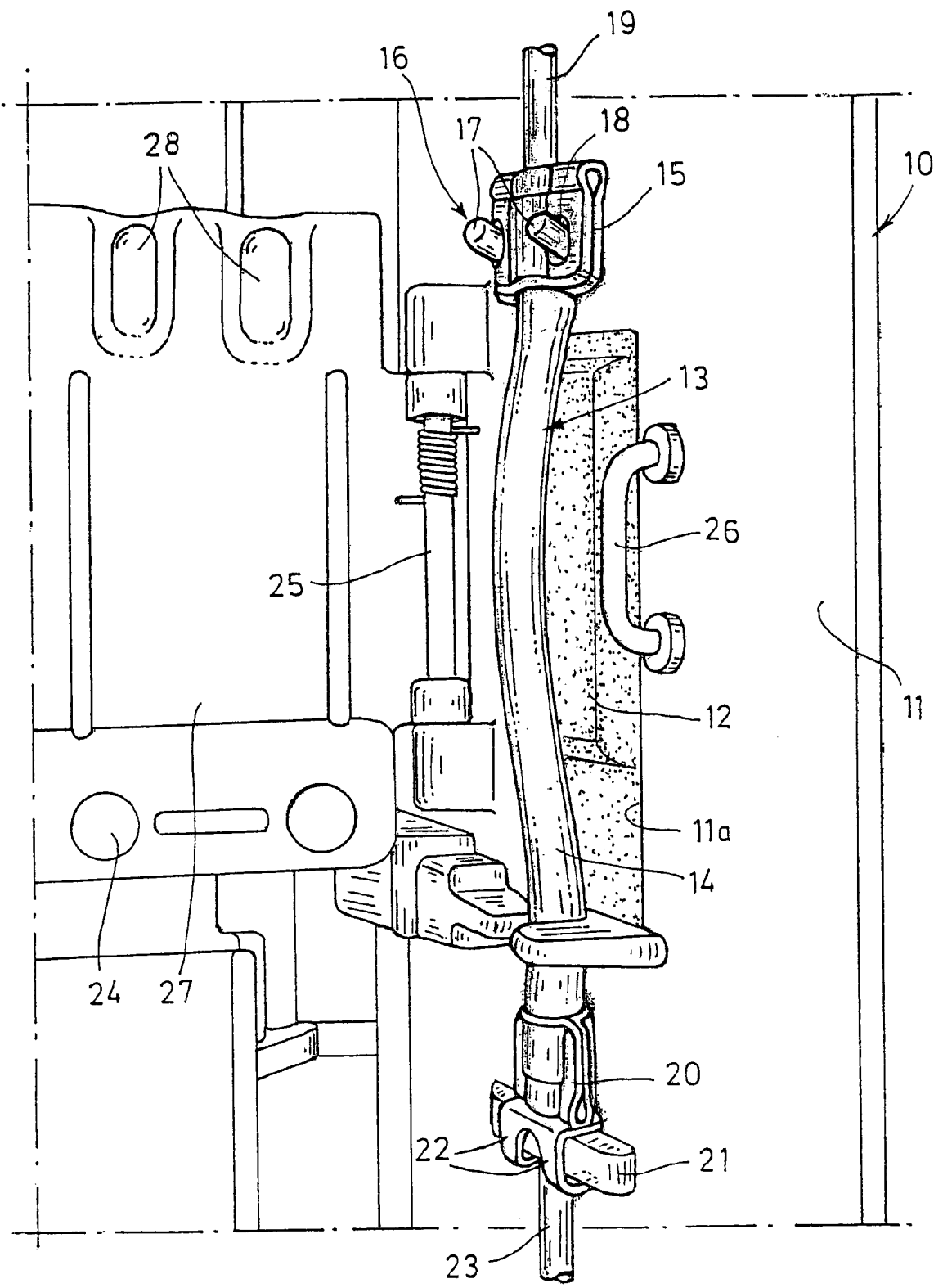
FIG. 1—is a perspective view of a part of the infusion pump with a housing and a pump hose exchangeably fastened thereto, FIG. 2—is a schematic vertical section through the upper holder and the transition piece fastened thereto, FIG. 3—is a front view of the pump hose fastened to the housing, and FIG. 4—is a perspective view of the upper transition piece prior to being fastened to the hose part of the pump hose.

The infusion pump illustrated in FIG. 1 comprises a housing 10 generally designed similar to the housing of the infusion pump of DE 8406203 U1. In a front wall 11 of the housing 10, an opening 11a is provided behind which a pump finger mechanism 12 of a finger pump (not illustrated) is arranged. The finger pump comprises numerous sequentially arranged fingers which are pressed one after the other from top to bottom against the pump hose and compress the same, so that the liquid contained therein is transported peristaltically from top to bottom. The pump finger mechanism 12 is covered by an elastic cover.

Figure 2:
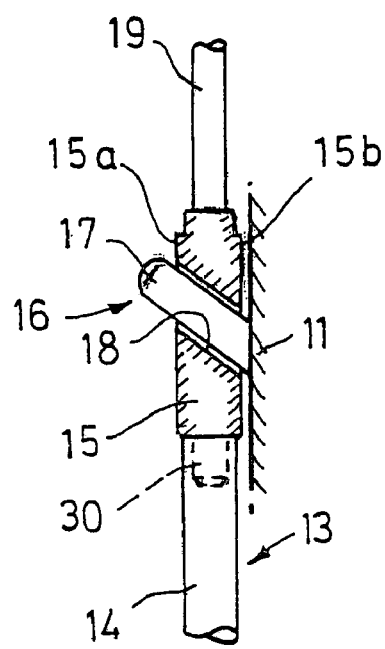

A pump hose 13 is installed in front of the opening 11a. The pump hose 13 comprises a length 14 of soft elastic hose, preferably made of silicone. For example, the length may be about 90 mm, the inner diameter 4 mm, and the outer diameter 6 mm. Fastened at the upper end of the length 14 of hose is an upper transition piece 15. This transition piece 15 is hung into an upper holder 16 of the housing 10. This holder 16 has two pins 17 arranged side by side and on the same level, projecting obliquely upward from the front wall 11 of the housing, as illustrated in FIG. 2. The transition piece 15 has two channel-shaped holes 18 extending obliquely upward, the axis thereof extending at the same angle as that of the pins 17. The transition piece 15 is connected with a supply hose 19 of flexible plastic material.

The transition piece has a front side 15a and a rear side 15b. The rear side 15b faces the front wall 11 of the housing. If the transition piece were mounted such that its front side 15a faced the front wall 11 of the housing, the transition piece would not flatly abut on the front wall 11 of the housing, but would project obliquely therefrom.

Accordingly, at least one of the holders cooperates with the associated transition piece by at least a combination of an oblique pin and an oblique hole to be slipped thereon, the pin and the hole being inclined the same with respect to the longitudinal axis of the installed pump hose.

With the pump hose installed properly, the oblique pin fits into the hole that has the same inclination so that the transition piece flatly abuts on the housing. When the transition piece is improperly applied to the housing, the transition piece is orientated obliquely with respect to the housing so that a bulge is caused in the hose, thereby impeding or preventing the door from being closed. Thus, an orderly operation of the pump is made impossible when the hose is placed improperly (rear up front). A construction according to certain aspects of the invention, serves to reduce improper placement of the pump hose.

In an exemplary embodiment, the at least one oblique pin is formed at the holder and the at least one oblique bole is formed in the transition piece. Further, in a preferred embodiment of the invention, two parallel pins are provided at the holder and two parallel holes are provided in the transition piece. Yet, it is also possible to provide the pin at the transition piece and the hole in the holder.

The hole is not a mere opening in a flat plate, but a cylindrical channel extending obliquely to the central plane of the transition piece.

The lower end of the pump hose 13 is equipped with a lower transition piece 20 hooked into a holder 21 of the housing. The transition piece 20 has two hook-shaped locking clamps 22 embracing the holder 21. The holder 21 is a transverse bar formed to the front wall 11. The bar has an opening for the passage of the discharge hose 23 connected to the transition piece 20. The transition pieces 15, 20, together with the length 14 of hose, form the pump hose 13. Together with a supply hose 19 and a discharge hose 23, the pump hose 13 forms a hose set which is a disposable article replaced after use.

A door 24 is provided at the housing 10 as a counterbearing for the pump hose 13, the door being adapted to be swiveled about a vertical axis 25 and being locked at a closing member 26. The door 24 is arranged opposite the pump finger mechanism 12 and has an abutment surface 27 where the length 14 of hose is compressed by the pump finger mechanism 12. Above the abutment surface 27, the door 24 has recesses 28 for receiving the ends of the pins 17 of the holder 16.

Thus, according to an exemplary embodiment of the invention, both holders are of different construction, each of the two transition pieces being adapted to the construction of the associated holder. In this manner, top and bottom of the pump hose cannot be interchanged, since the lower transition piece does not mate with the upper holder and the upper transition piece does not mate with the lower holder.

Figure 3:
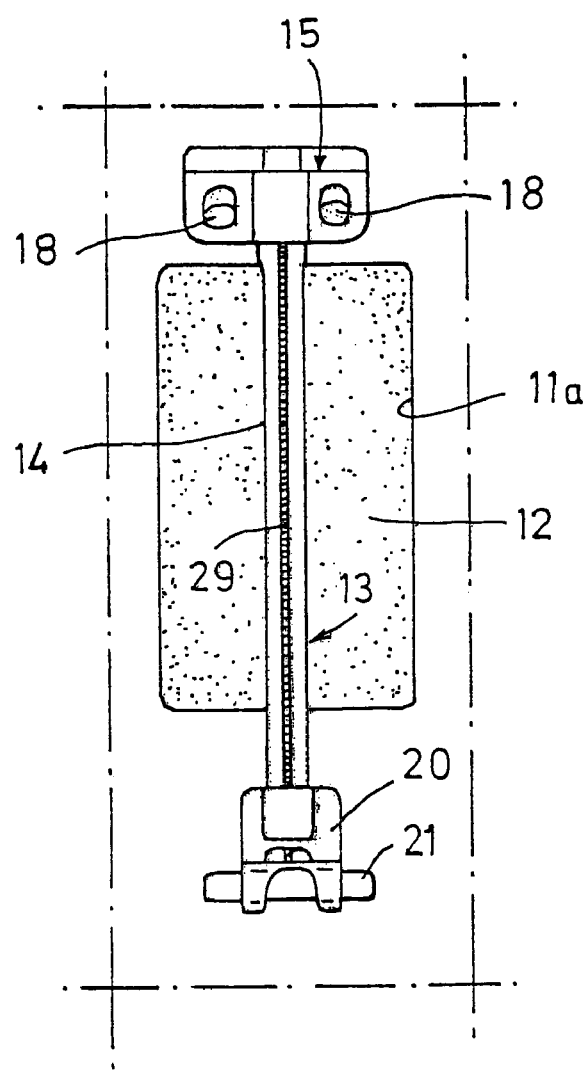

FIG. 3 illustrates a front view of the properly installed pump hose 13. At the front side of the length 14 of hose that is visible to the user when the door 24 is open, a longitudinal color strip 29 is provided. The color strip may consist of food colors applied as by rolling on to hose during extrusion prior to the hardening of the hose material. The color strip 29 would make visible a twisting of the lower transition piece 20 by 360° in the event that the length 14 of hose were helically twisted.

In an exemplary embodiment, the pump hose is provided with a longitudinal color strip. In this manner, torsional twisting of the pump hose can easily be recognized visually.

Figure 4:
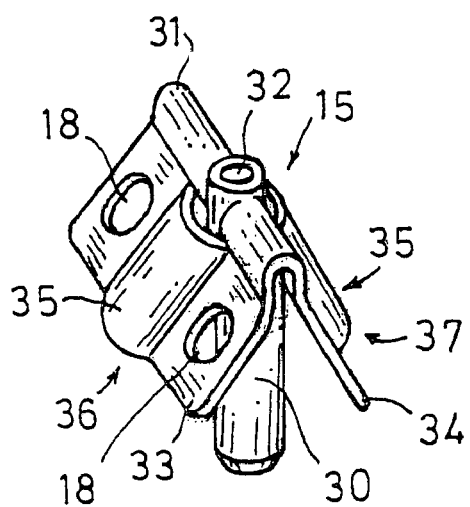

In FIG. 4, the transition piece 15 is illustrated in its open state prior to its being mounted to the length 14 of hose. The transition piece 15 has a tubular pin 30 onto which the length 14 of hose can be slipped. A transverse hinge portion 31 extends at an end of the tubular pin 30, which projects towards opposite ends from the upper opening 32 of the tubular pin 30. The supply hose 19 is inserted into the upper opening 32 and glued. The hinge portion 31 is bent in U-shape and flanges 33 and 34 project from its legs, respectively. The flanges 33, 34 each include a tunnel 35 and form two half shells 36, 37 whose flanges 33, 34 can be pressed against each other and whose tunnels 35 then combine to a cylindrical channel coaxially enclosing the tubular pin 30. The tubular pin 30 forms an inner support for the end of the length 14 of hose clamped and fixed by the half shells 36, 37.

The invention addresses a problem of improving the attachment of transition pieces to a pump hose. Where the soft elastic pump hose, often made of silicone, cannot be glued or welded to other components, a mechanical connection between these parts has been found to be required. Presently, the end of the pump hose is slipped onto a tubular pin of the transition piece. Subsequently, a tensioning ring is placed around the slipped-on end of the pump hose to fix the same on the tubular pin in a sealing manner.

The two transition pieces 15 and 20 consist of hard plastic material such as ABS. They are fixed in the final position by ultra sound or heating stamps wherein they press the length of hose onto the hard tubular pin. The entire transition piece 15 illustrated in FIG. 4 is an integral plastics part that may be produced as an injection molded part. The hinge portion 31 radially abuts the upper end of the tubular pin 30 from opposite sides and passes into the same.

Thus, what has been disclosed in one embodiment is an infusion pump with a pump hose such that both in case of an axial twist of the transition pieces with respect to each other and in case of an erroneous placement of the pump element (rear up front), the error is immediately visible and an operation of the pump becomes impossible, respectively.

In one embodiment of the invention, a pump hose is provided with transition pieces at both ends, which has a high tensile strength and a substantially improved compression strength and is simple to manufacture.

Variations And Equivalents

Spatial references such as "bottom", "top", "front", "back", "lower", "upper", "under", and "central" are for purposes of illustration only, relative to the figures shown and are not limited to the specific orientation of the structure or movement directions as described.

Although only a few exemplary embodiments of this invention have been described in detail above, those skilled in the art will readily appreciate that many other modifications are possible in the exemplary embodiments without materially departing from the novel teachings and advantages of this invention. Accordingly, all such modifications are intended to be included within the scope of this invention as defined in the following claims.

What is claimed is:

1. An infusion pump comprising:
   a pump hose (13) having two transition pieces (15, 20) at opposite ends, respectively, of the pump hose;
   a housing (10) accommodating a pump finger mechanism (12) and having two holders (16, 21) for fastening the two transition pieces (15, 20), a door (24) provided at the housing (10) and forming a counter bearing for supporting the pump hose (13); and
   wherein at least one of the holders (16) mates with at least one associated transition piece (15) of the two transition pieces (15, 20) via at least a combination of an oblique pin (17) and an oblique hole (18) to be slipped onto the oblique pin, the pin (17) and the hole (18) being inclined the same with respect to a longitudinal axis of the placed pump hose (13).

2. The infusion pump of claim 1, wherein the oblique pin (17) is provided at the holder (16) and the oblique hole (18) is provided at the associated transition piece (15).

3. The infusion pump of claim 2, wherein the at least one holder (16) has two parallel oblique pins (17) and the associated transition piece (15) has two parallel holes (18).

4. The infusion pump of claim 1, wherein the at least one holder (16) has two parallel oblique pins (17) and the associated transition piece (15) has two parallel holes (18).

5. The infusion pump of claim 1, wherein the door (24) is provided with recesses (28) for receiving the ends of the pins (17).

6. The infusion pump of claim 1 wherein another transition piece (20) of the two transition pieces (15, 20) comprises a locking clamp (22) engaging over a web of the housing (10).

7. The infusion pump of claim 1, wherein the pump hose (13) has a longitudinal color strip (29) for detecting hose twisting.

8. The infusion pump of claims 1, 2, 3, 4, 5, 6, or 7, wherein the pump hose further comprises:
   a length of hose (14) with the two transition pieces (15 and 20) at opposite ends of the length of hose (14), wherein the at least one associated transition piece (15) of the two transition pieces (15 and 20) has two half shells (36, 37) connected by a hinge portion (31), a tubular pin (30) projecting from the hinge portion (31), and the half shells (36, 37) having flanges (33, 34) adapted to be abutted against and connected with each other, the flanges clampingly enclosing the end of the length of hose (14) slipped on the tubular pin (30).

9. The pump hose of claim 8, wherein the associated transition piece (15) is an integral plastic part.

10. A transition piece (15) for clampingly holding an end of a length of hose (14), the transition piece (15) comprising:

two half shells (36, 37) connected by a hinge portion (31), the half shells (36, 37) having flanges (33, 34) adapted to be abutted against and connected with each other;

a tubular pin (30) projecting from the hinge portion (31); and wherein the flanges clampingly enclose the end of the length of hose (14) slipped on the tubular pin (30).

11. The transition piece (15) of claim 10, wherein the flanges of the half shells each define a tunnel portion generally aligned with each other to form a channel when the flanges are abutted and connected to each other, the channel sized for clamping engagement with a end of a tube slipped onto the tubular pin.

12. The transition piece (15) of claim 10, further comprising;

an opening sized for receiving a tubing, the opening interconnecting through the hinge to the tubular pin so that a tubing received in the opening is in fluid communication with a hose slipped onto the pin.

13. The transition piece (15) of claim 12, wherein the tubing is sealingly attached to the opening.

14. The transition piece (15) of claims 10, 11, 12 or 13, wherein the transition piece is an integral plastic part that is bendable about the hinge.

15. The transition piece (15) of claim 14, wherein the flanges are connectable to each other by plastic welding.

16. The transition piece (15) of claim 14, wherein the plastic of the transition piece is relatively harder than the hose.

17. A transition piece (15) comprising:

a tubular pin (30) sized for inserting into an end of a hose (14);

a hinge portion (31) integrally formed attached transverse to the tubular pin (30);

at least two shells (36, 37) integrally formed connected to the hinge portion (31) projecting adjacent to the tubular pin (30), wherein the shells are pivotable on the hinge to clamp the end of the hose onto the tubular pin.

18. The transition piece (15) of claim 17, wherein the at least two shells each further comprise an integrally formed flange defining an tunnel portion so that a tubular clamping channel is formed between the flanges when the shells are pivoted on the hinge and the flanges are abutt against and connected to each other.

19. The transition piece (15) of claim 17, further comprising;

an opening sized for receiving a tubing, the opening interconnecting through the hinge to the tubular pin so that a hose slipped onto the tubular pin is in fluid communication with the opening.

20. The transition piece (15) of claim 19, wherein the opening is connectable to a tubing so that the tubing and the hose are interconnectable into fluid communication through the transition piece.

21. A pump hose comprising:

a length of hose (14) with two transition pieces (15 and 20) at opposite ends of the length of hose (14), wherein at least one associated transition piece (15) of the two transition pieces (15 and 20) comprises two half shells (36, 37) connected by a hinge portion (31), a tubular pin (30) projecting from the hinge portion (31), and the half shells (36, 37) having flanges (33, 34) adapted to be abutted against and connected with each other, the flanges clampingly enclosing the end of the length of hose (14) slipped on the tubular pin (30).

22. The pump hose of claim 21, wherein the at least one associated transition piece (15) of the two transition pieces (15, 20) further comprises at least one oblique hole inclined at an oblique angle relative to the tubular pin.

* * * * *